United States Patent [19]

Henley et al.

[11] Patent Number: 5,010,876

[45] Date of Patent: Apr. 30, 1991

[54] ARTHROSCOPIC SURGICAL PRACTICE

[75] Inventors: Gary D. Henley; Larry B. Milner, both of Yukon; Clifford A. Dowdy, Oklahoma City, all of Okla.

[73] Assignee: Smith & Nephew Dyonics, Inc., Andover, Mass.

[21] Appl. No.: 869,595

[22] Filed: Jun. 2, 1986

[51] Int. Cl.$^5$ .............................................. A61B 1/04
[52] U.S. Cl. ........................................ 128/6; 358/98; 206/438
[58] Field of Search ..................... 128/3, 4, 5, 6, 7, 11; 358/98; 206/438

[56] References Cited

U.S. PATENT DOCUMENTS

| | | | |
|---|---|---|---|
| 3,426,749 | 2/1969 | Jephcott | 128/11 |
| 4,519,391 | 5/1985 | Murakoshi | 128/4 X |
| 4,522,196 | 6/1985 | Cunningham et al. | 128/4 |
| 4,590,923 | 5/1986 | Watanabe | 128/6 |

Primary Examiner—William H. Grieb
Attorney, Agent, or Firm—Laney, Dougherty, Hessin & Beavers

[57] ABSTRACT

Method and apparatus for providing a disposable, sterile cable connector and camera head for use in endoscopic surgery. A novel camera head design is disclosed in combination with the requisite connector cable, and such camera head/cable is adapted for initial sterility and sterile packaging for subsequent singular use and disposal after surgery. The camera head consists of a charge-coupled device type of image sensor assembled in a compact camera head of a type that can be completely sterilized, sealed and packaged for prolonged shelf storage and eventual disposable usage.

9 Claims, 3 Drawing Sheets

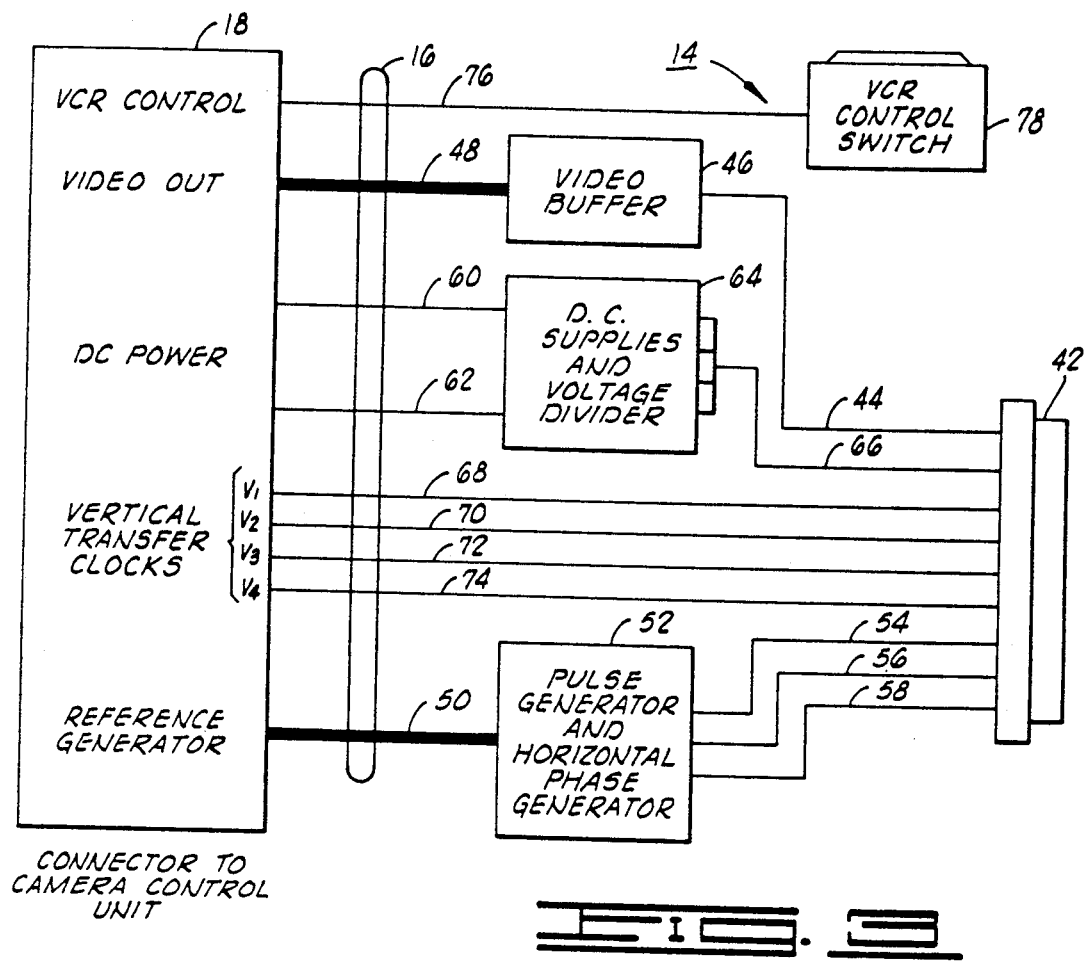
FIG. 3
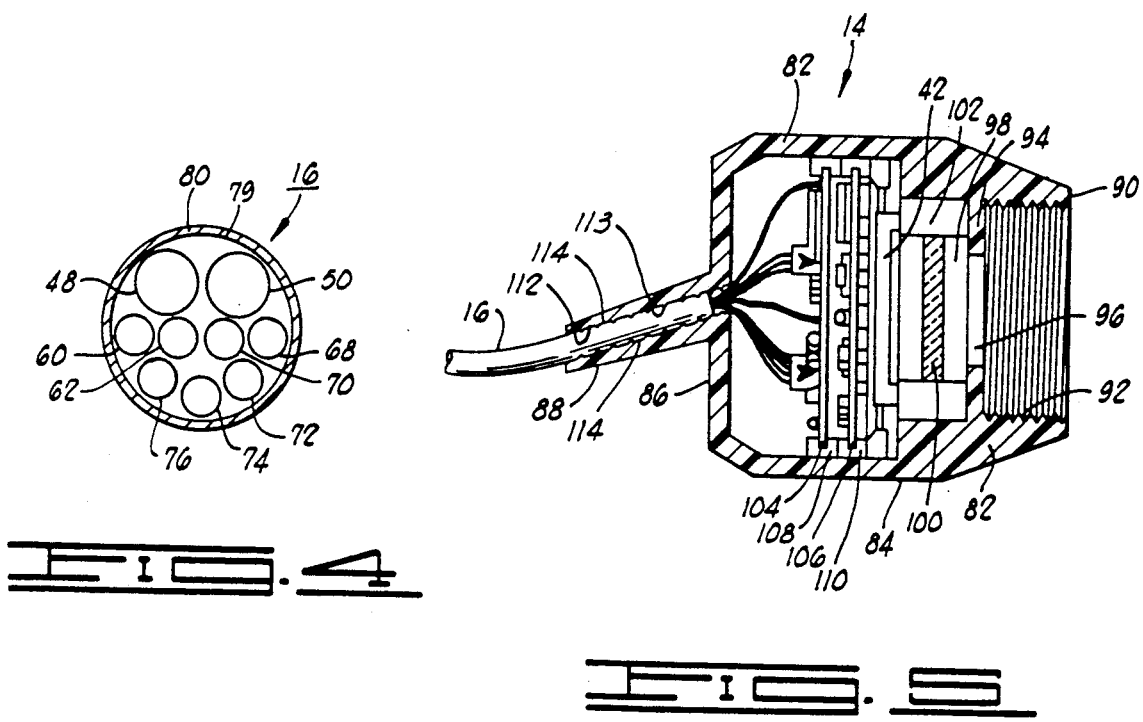
FIG. 4
FIG. 5

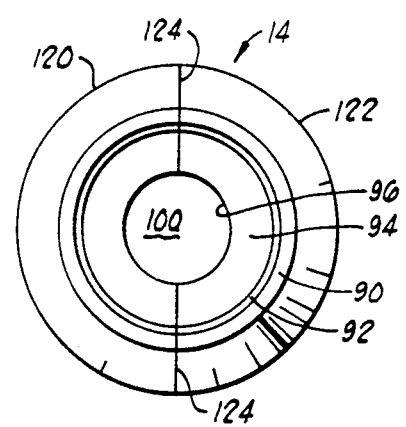
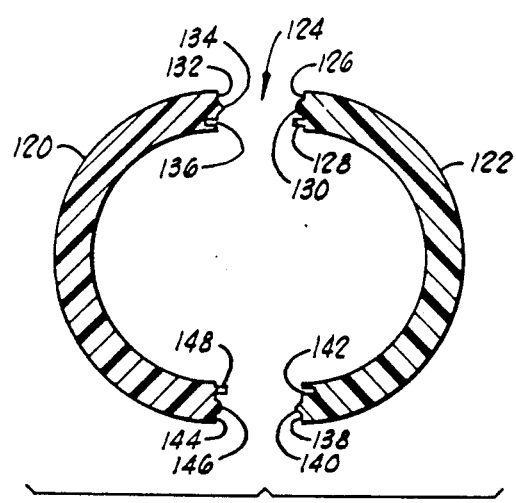
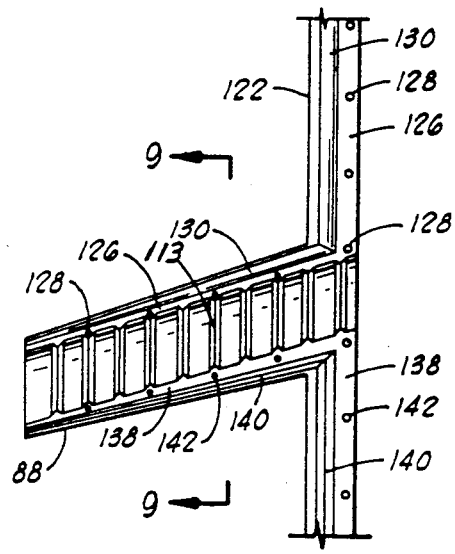
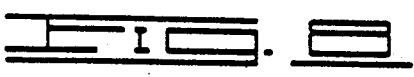
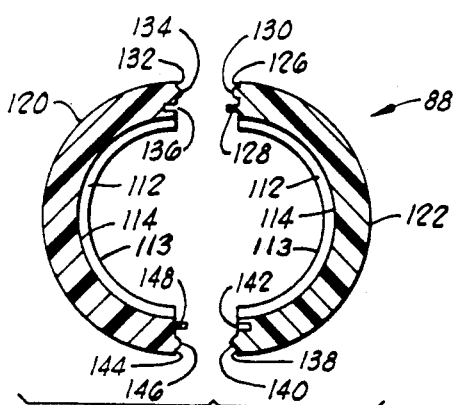
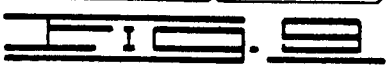
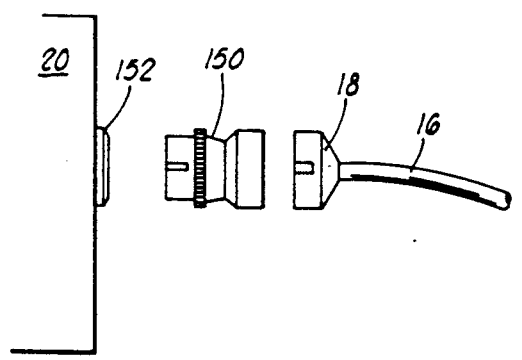
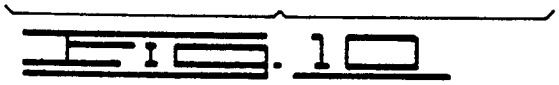

ARTHROSCOPIC SURGICAL PRACTICE

BACKGROUND OF THE INVENTION

1. Field of the Invention

The invention relates generally to endoscopic surgical methods and apparatus and, more particularly, but not by way of limitation, it relates to improvements in methods of arthroscopic surgery wherein disposable video imaging devices may be utilized to increase sterilization effectiveness while reducing overall equipment costs.

2. Description of the Prior Art

The prior art includes numerous types of endoscopic viewing device as they have been used down through the years for observation of internal passages and organs of the body. Thus, flexible, scopic instruments of differing diameters and lengths serve various purposes as proctoscopes, cystoscopes and the like, size and length being generally dictated by intended usage. More recently, developments in solid state imaging devices and other television pickup methods and advances in fiber optics light transmission have led to a number of new techniques wherein a selected form of imaging device is used in combination with a selected endoscope to enable monitored exploration of an internal part or wound with attendant probing and/or corrective instrument functioning in response to the visual picture as derived and reproduced on a suitable monitor. What is now generally referred to as arthroscopic surgery has come into being and presently enjoys widespread success using the various scope instruments with image sensory devices to direct surgical instruments.

SUMMARY OF THE INVENTION

The present invention relates to a new use of prior method and apparatus as well as improvements in component devices used for endoscopic surgery. As usually required in such surgery, there is a camera control unit, recorders, monitor units and a suitable light source as used in conjunction with the scope instrument. In the present invention, it is proposed to provide a pre-packaged, sterilized camera/connector unit in the form of a connector plug, suitable length of connector cable and fluid-tight camera housing carrying a solid state image sensor. For a single surgical procedure, the pre-packaged assembly can be opened and plugged into the camera control unit, and the arthroscope or other scope instrument to be utilized is then attached to the camera head. The equipment is then ready for a surgical procedure which, upon completion, will enable discard of the camera/connector unit and effective dismissal of the unit from further surgical application.

Therefore, it is an object of the present invention to provide a sterile arthroscopic surgery imaging device that exhibits greater readiness for use and reliability of sterility.

It is also an object of the present invention to enable overall cost reduction in arthroscopic surgery practice.

It is yet another object of the invention to provide a disposable surgical imaging device that need not be subjected to more than one initial potentially dangerous and damgaging sterilization procedure.

It is still further an object of the present invention to provide a method for providing sterile imaging devices that is safer and more reliable.

Finally, it is an object of the present invention to provide a solid state imaging device that is compact and small in size while offering an absolute sterile condition through a surgical procedure with subsequent disposal.

Other objects and advantages of the invention will be evident from the following detailed description when read in conjunction with the accompanying drawings which illustrate the invention.

BRIEF DESCRIPTION OF THE DRAWINGS

FIG. 3 is a block diagram of the electronic components of the disposable unit shown in FIG. 2;

FIG. 4 is a sectional illustration showing individual conductor array of the connector cable;

FIG. 5 is a view in vertical section through the camera head of the present invention; FIG. 6 is a front view in elevation of the camera head of FIG. 2; FIG. 7 is a sectional showing through the camera housing illustrating the mating engagement of the housing frame; FIG. 8 is an enlarged view illustrating the base portion and strain relief sleeve of one-half of a camera housing; FIG. 9 is a section taken through the strain relief sleeve at lines 9—9 of FIG. 8; and FIG. 10 is an illustration of an adaptor that may be utilized in connecting the connector cable to the camera control unit.

DETAILED DESCRIPTION OF THE INVENTION

Figure 1:
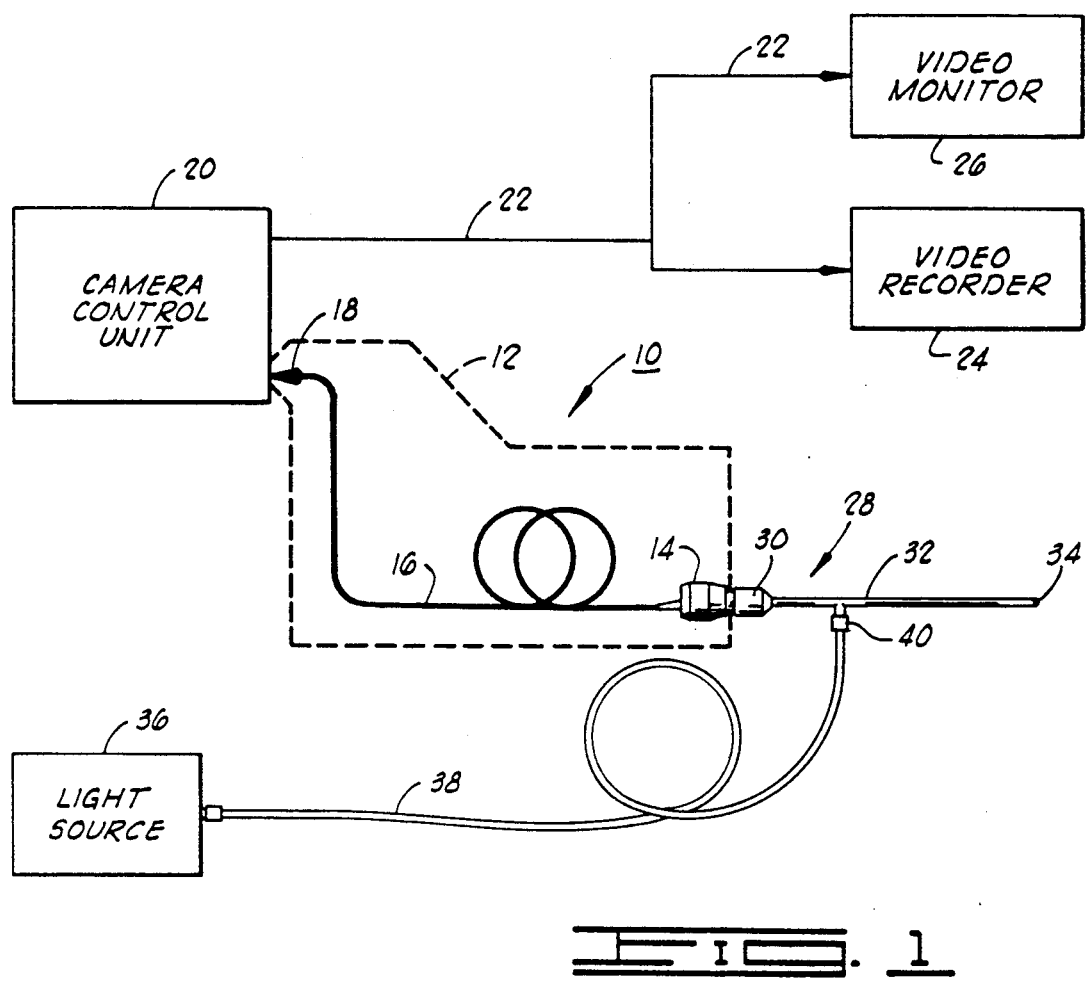
FIG. 1 is a block diagram of equipment utilized in endoscopic surgical practice and including the prepackaged disposable imaging device of the present invention.
Figure 2:
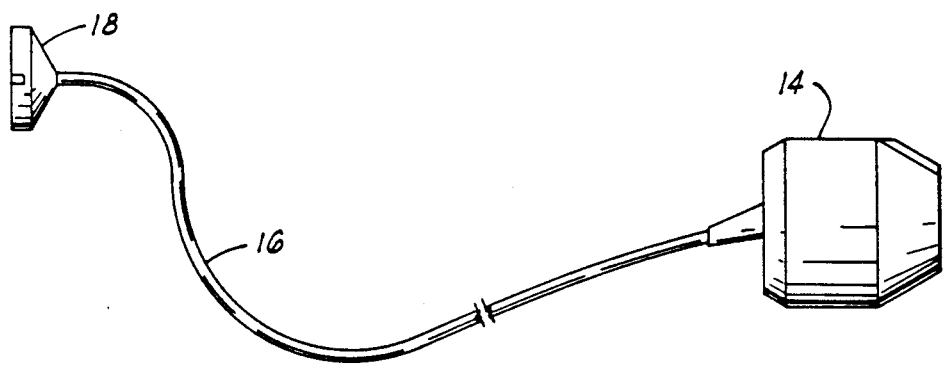
FIG. 2 is a view in elevation of a camera and connector cord unit constructed in accordance with the present invention.

FIG. 1 illustrates equipment utilized in the performance of endoscopic surgery, including the sterile connector/camera unit 10 as contained in a sterile pack, illustrated generally by dash line 12. The unit 10 consists of a camera head 14, see also FIG. 2, connected by means of a cable 16 and plug connector 18 to a camera control unit 20. The camera control unit 20 serves as primary power and control source providing operational voltage supply to camera head 14 while also providing video and scanning output voltages via line 22 for input to a respective video recorder 24 and video monitor 26.

Light input to camera head 14 is provided by means of a scope instrument such as an arthroscope 28. Arthroscope 28 is directly connected to camera head 14, i.e. a scope head 30 is affixed by threaded connection into the front of camera head 14. The arthroscope 28 consists primarily of an elongated tube 32 that carries an objective lens and a plurality of optical fibers terminating at a viewing tip 34. Thus, any view apparent at tip 34 is conducted by fiber optics for presentation to the imaging surface within camera head 14, as will be further described. Intermediate along tubing 32 is a birefringent interface that allows introduction of an external light source through the viewing tip 34. Thus, a suitable light source 36 provides output through a plurality of fibers of an optical cable 38 which is plugged in at a junction connector 40 wherein reflection from the birefringent reflector in tubing 32 delivers light on the subject through the viewing tip 34.

The camera control unit 20 and light source 36 are standard equipment and suitable units are commercially available from Dyonics Corporation of Andover, Mass. Also, such as the arthroscope 28 and light source and conductor accessories are available from the Dyonics Corporation. Ancillary equipment such as video monitor 26, video recorder 24 and other support devices may be acquired from any of various commercial suppliers, e.g. Panasonic Corporation is a major supplier of high performance video equipment.

FIG. 3 illustrates the connector cable 16 and electronics of camera head 14. An image sensor 42 within camera head 14 provides optical pickup and output of video electrical data. The image sensor 42 may be a suitable charge-coupled device, for example an Amperex Type KX-1020. Video signal output via a lead 44 is applied through a video buffer 46 for output via a coaxial cable 48 within the cable connector 16. Scan frequency output from the camera control unit 20 (FIG. 1) provides a reference generator input on a coaxial cable 50 of cable 16 to a stage 52 in camera head 14 which functions to generate frame and horizontal phase pulse output. The pulse generator 52 provides output via leads 54, 56 and 58 to the image sensor 42. The video buffer 46, pulse generator circuitry 52 and D-C control circuitry may be constructed of selected types of transistor logic integrated circuits of known type.

D-C power from camera control unit 20 is supplied via leads 60 and 62 to a D-C supply and voltage divider stage 64 in camera head 14. Voltage divider of supply stage 64 then provides output via lead 66 of a D-C bias voltage to image sensor 42. Vertical transfer clock pulses from camera control unit 20 are successively output on respective leads 68, 70, 72 and 74 for direct connection to the image sensor 42. Finally, a lead 76 provides switch indication from a recorder control switch 78 for control application through camera control unit 20. The switch 78 may be a suitable form of push button switch, e.g. a membrane switch that is actuable through the sealed housing of camera head 14. As shown in FIG. 4, the cable 16 includes 2 coaxial cables 48 and 50 while the remaining seven leads 60, 62, 68, 70, 72, 74 and 76 are 30-gauge wires. The cable is contained in a braided shield 79 and sheathing 80 of a suitable resilient cable material that is susceptible of sterilization treatment, e.g. a polyethylene sheathing.

Referring to FIG. 5, the camera 14 is preferably formed in unitary or suitably continuous manner, thus aiding in keeping sterilization, and it is designed to be compact and readily sealable against fluid incursions. Thus, the camera housing 82 may be formed of a suitable plastic, e.g. a styrene polymer such as ABS. The housing 82 is preferably formed with a side wall 84, a base portion 86 and a strain relief sleeve portion 88 extending generally axially therefrom. The forward part of side wall 84 terminates at a rim 90 defining a threaded bore 92 which is adapted to receive threaded connection of the standard size arthroscope or other endoscopic instrument. There are a limited few such standard sizes and selected adaptors enable interchangeability. Housing 82 is further formed with an annular shoulder 94 which defines an aperture 96 that allows light transmission through a filter chamber 98 to the image sensor 42. A linear infrared filter 100 may be disposed in filter chamber 98 and sealingly retained therein by means of a resilient mounting ring 102. An objective lens (not shown) projecting image light through filter 100 onto sensor 42 is retained in the associated scopic instrument.

Electronic components are arrayed on miniature circuit boards 104 and 106 as they are retained by respective molded insert locators 108 and 110. The individual wires and coaxial cable connections from cable 16 are connected to the respective circuit boards 104, 106 as cable 16 is clamped within the strain relief sleeve 88 to effect a tight seal. The sleeve 88, to be further described below, includes a plurality of spaced ridges 113 about its inner circumfery and, on assembly, a suitable sealant 112 is applied in the grooves 114 between respective ridges 113 and tightly secured in surround of cable 16 to effect a fluid-tight seal suitable for withstanding leakage during normal sterilization procedures.

FIG. 6 illustrates a front view of the camera head 14 as it is unitarily molded into a two-halves structure from a suitable plastic selected for resistance in the particular environment to be encountered. Thus, the camera head consists of a first housing half 120 and a second housing half 122 joined along a seam 124. The moldings form annulus 94 defining aperture 96 through which light reflected from the subject source is presented through filter 100 to the image sensor 42 (FIG. 5). An objective lens (not shown) projecting subjective light through filter 100 is an integral component of the arthroscope or other endoscope used in conjunction with the camera head. The scope instrument is secured in outer rim 90 within threaded bore 92.

As shown in FIG. 7, the two housing halves 120 and 122 are joined along seam 124 by facings which include both a dowel/pin arrangement and a ring/point sealing engagement. Thus, the upper joinder face 126 of half 122 includes a series of dowel/pins 128 as well as an O-ring formation 130 extending therealong. The upper face 132 of half 120 includes a point or ridge formation 134 and series of dowel holes 136 for mating engagement when the face halves are joined together in sealed formation to form seam 124. The seam 124 along the lower side of camera head 14 is similar but opposite as the dowel and ring/point surfaces are reversed. That is, bottom face 138 of half 122 includes a ridge line 140 and series of dowel holes 142, and lower face 144 of half 120 includes a semi-circular ring line 146 and series of dowel/pins 148.

This structure is shown to better advantage in an enlarged rear section of the housing half 122 as shown in FIG. 8. This view illustrates the manner in which the housing half faces continue clear around the camera housing 14 and extend outward along the strain relief sleeve 88 to further aid in bringing about a sterile, fluid-tight seal as between the connector cable 16 and the components within the camera housing. FIG. 9 illustrates the ring/point and dowel/pin arrangement along sleeve 88. In assembly, a suitable sealant such as a silicon latex compound is applied within the grooves 114 of sleeve 88 whereupon the halves 120 and 122 are then joined together with sleeve 88 (ridges 113) tightly seizing cable 16 therein. A selected bonding agent is applied to the respective upper joinder faces 126, 132 and lower joinder faces 138, 144 to secure the camera head 14 with seam 124 consolidated on both top and bottom.

FIG. 10 illustrates an alternative that may be required in connecting the cable 16 and plug connector 18 into the particular camera control unit 20. In some cases, a suitable adaptor 150 may be utilized in effecting the connection through connector receptacle 152 to the camera control unit 20. There are several standard sizes of connectors which the various control unit manufacturers utilize, and utilization of adaptor connectors 150 will provide total interchangeability.

In operation, any problems as to sterilization maintenance, operability and the like are overcome initially when, upon assembly, the unit 10 is tested, completely sterilized and encapulated in a suitable sterile pack. Sterilization may be by immersion in ethylene oxide (ETO) or other recognized and acceptable practice. In standard procedure, the unit 10 in sterile form would be wrapped in sterile cotton cloth and then enclosed in a suitable transparent or translucent paper or plastic bag capable of maintaining tight seal and sterility over a long period of time. Such disposable camera units 10 are then available for shipping and shelf storage at operating facilities in whatever volume might be foreseen. The attendant electronics such as camera control unit 20 and the recording and monitoring hardware is of permanent installation and maintained in readiness in the endoscopic surgical operating room. In like manner, the light source 36 and fiber optics cable 38 with attendant control structure and arthroscope 28 and/or other scope instruments is kept in readiness. When a surgical operation is to be performed, an attending nurse need only select from storage a sterile pack 12 containing the camera unit 10 which can then be unwrapped and connected between the camera control unit 20 and the operating position by attachment of camera 14 to the arthroscope 28. Cable 16 may be of about 12 feet in length to offer ample slack for movement about an operating area without interference. Similarly, the fiber optics cable 38 is of sufficient length to enable free access and movement. The arthroscopic or other endoscopic surgery is then performed through completion whereupon the patient is removed to a post-operative area and the camera unit 10, i.e. camera head 14 and cable 16, may be disconnected and disposed of as far as further surgical use is concerned.

The foregoing discloses novel equipment and procedure that enables greater assurance of surgical sterility while eventually serving to reduce the cost overall of performing arthroscopic surgery. The concept of a disposable camera is attractive to the attending physician and nurse staff for not only a decrease in the cost of operations, but also the provision of greater assurance as to sterility in and around the operating area. Thus, sterilization of equipment at a central agency enables elimination of dangerous and even poisonous sterilization materials from the operating area and related laboratories. In addition, the disposable usage of camera units provides an operative tool that is assured to be of maximum acuity and resolution without requiring additional tuning or peaking operations.

The practice also provides greater assurance against failure of individual camera components, electrical connections and the like. One of the chief sources of failure with the prior surgical camera units is the multi-conductor connector cable as repeated sterilization procedures can cause opening of one or more of the diminutive conductors encased therein. When this occurs, the entire operating procedure must be stopped or slowed as new camera equipment (if available) is interconnected and any additional sterilzation procedures are effected. The present method obviates such emergency measures as a new, sterile connector/camera unit is unveiled for use with each operation.

Changes may be made in combination and arrangement of elements as heretofore set forth in the specification and shown in the drawings; it being understood that changes may be made in the embodiments disclosed without departing from the spirit and scope of the invention as defined in the following claims.

What is claimed is:

1. In combination with video monitor, camera control unit, light source and scope instrument for imaging surgical activity, a disposable camera device comprising:
   an imaging device including control circuitry;
   a sterilized connector cable of pre-selected length connected to said control circuitry and extending to an external plug connector for connection to said camera control unit;
   a sterilized camera housing means for containing said imaging device and control circuitry in sealed, fluid-tight disposition, said camera housing means consisting of a generally cylindrical housing bisected to define a first half-housing having sidewall, base portion and sleeve portion, and a second half-housing having sidewall, base portion and sleeve portion for mating engagement as said first and second half-housings are juxtaposed; and
   sterile container means for enclosing and maintaining said camera housing means and connector cable in sterile storage until opening of the container means for exposure during usage.

2. An article of manufacture comprising:
   an imaging device including electronic control circuitry;
   a sterilized connector cable having multiple conductor and being of pre-selected length having a plug connector on one end and having the other end connected to said control circuitry;
   a sterilized housing means retaining said imaging device and control circuitry in fluid-tight, sealed connection to said connector cable, said housing means consisting of a generally cylindrical housing bisected to define a first half-housing having side wall, base portion and sleeve portion, and a second half-housing having side wall, base portion and sleeve portion for mating engagement as said first and second half-housings are juxtaposed; and
   isolation means maintaining said imaging device, connector cable and housing means sterile until disposable usage.

3. An article of manufacture as set forth in claim 2 which is further characterized to include:
   a first joinder face including sealing means formed along the bisection on the first half-housing; and
   a second joinder face including sealing means formed along the bisection on the second half-housing.

4. An article of manufacture as set forth in claim 3 wherein said sealing means comprises:
   a ring formation extending along one of said first and second joinder faces; and
   a mating ridge formation extending along the other of said first and second joinder faces.

5. An article of manufacture as set forth in claim 4 which further comprises:
   plural doweling pins and holes disposed in spaced, mating positions along each of said first and second joinder faces.

6. An article of manufacture as set forth in claim 3 which further includes:
   plural doweling pins and holes disposed in spaced, mating positions along each of said first and second joinder faces.

7. An article of manufacture as set forth in claim 2 which further includes:
   high temperature, fluid-tight sealing compound applied between the connector cable and said first and second half-housing sleeve portions.

8. An article of manufacture as set forth in claim 2 wherein said cylindrical housing comprises:

a light entry bore formed generally axially between said first and second half-housing sidewalls in alignment with said imgaging device; and means for securing a scope instrument to said housing in alignment with said light entry bore.

9. An article of manufacture as set forth in claim 8 wherein said means for securing comprises:

threads formed in said light entry bore for receiving said scope instrument in secure threaded engagement.

* * * * *